(12) United States Patent
Sherlock

(10) Patent No.: US 10,697,153 B2
(45) Date of Patent: Jun. 30, 2020

(54) WORK MACHINE GRADING CONTROL SYSTEM

(71) Applicant: Deere & Company, Moline, IL (US)

(72) Inventor: Lance R. Sherlock, Asbury, IA (US)

(73) Assignee: Deere & Company, Moline, IL (US)

(*) Notice: Subject to any disclaimer, the term of this patent is extended or adjusted under 35 U.S.C. 154(b) by 214 days.

(21) Appl. No.: 16/029,845

(22) Filed: Jul. 9, 2018

(65) Prior Publication Data

US 2020/0011033 A1    Jan. 9, 2020

(51) Int. Cl.
| | | |
|---|---|---|
| *E02F 3/84* | (2006.01) | |
| *E02F 9/26* | (2006.01) | |
| *E02F 3/76* | (2006.01) | |
| *G01N 33/24* | (2006.01) | |
| *G01B 11/14* | (2006.01) | |
| *E02F 9/20* | (2006.01) | |

(52) U.S. Cl.
CPC ............ *E02F 9/262* (2013.01); *E02F 3/7609* (2013.01); *E02F 3/844* (2013.01); *G01B 11/14* (2013.01); *G01N 33/246* (2013.01); *E02F 3/841* (2013.01); *E02F 9/2041* (2013.01); *E02F 9/264* (2013.01)

(58) Field of Classification Search
CPC . E02F 3/84; E02F 3/844; E02F 9/2029; E02F 9/2041
USPC ...................................................... 172/2, 4.5
See application file for complete search history.

(56) References Cited

U.S. PATENT DOCUMENTS

| | | | |
|---|---|---|---|
| 4,194,574 A | | 3/1980 | Benson et al. |
| 4,630,685 A | * | 12/1986 | Huck, Jr. ................ E02F 3/845 172/2 |
| 5,815,826 A | | 9/1998 | Henderson et al. |
| 7,917,265 B2 | | 3/2011 | Kale et al. |
| 8,296,019 B2 | | 10/2012 | Kendrick |
| 8,612,103 B2 | * | 12/2013 | Nicholson ............... E02F 3/432 172/4.5 |

(Continued)

FOREIGN PATENT DOCUMENTS

WO    WO 2018051742 A1    6/2019

OTHER PUBLICATIONS

German Search Report issued in counterpart application No. 102019208302.1 dated Apr. 23, 2020 (08 pages).

*Primary Examiner* — Gary S Hartmann
(74) *Attorney, Agent, or Firm* — Joseph R. Kelly; Kelly, Holt & Christenson PLLC

(57) ABSTRACT

A mobile work machine includes a frame and a ground engaging element movably supported by the frame and driven by an engine to drive movement of the mobile work machine. The mobile work machine includes a movable element movably supported by the frame to move relative to the frame and an actuator coupled to the movable element to controllably drive movement of the movable element. The mobile work machine includes a sensor that detects an operation characteristic and generates a sensor signal, indicative of the operation characteristic and a grade control system that receives the sensor signal from the sensor and determines a spillage metric, based on the sensor signal. The mobile work machine also includes a control system that generates an actuator control signal based on the spillage metric. The control signal is indicative of a commanded movement of the actuator. The control system controls the actuator to perform the commanded movement.

20 Claims, 10 Drawing Sheets

(56) References Cited

U.S. PATENT DOCUMENTS

2016/0076224 A1    3/2016  Edara et al.
2020/0011029 A1*   1/2020  Sano .................... E02F 9/2045

\* cited by examiner

WORK MACHINE GRADING CONTROL SYSTEM

FIELD OF THE DESCRIPTION

The present description relates to earth moving operations. More specifically, the present description relates to an earth grading control system.

BACKGROUND

There are many different types of work machines. Some such work machines include agricultural machines, construction machines, forestry machines, turf management machines, among others. Many of these pieces of mobile equipment have mechanisms that are controlled by the operator in performing operations. For instance, a construction machine can have multiple different mechanical, electrical, hydraulic, pneumatic and electro-mechanical subsystems, among others, all of which can be operated by the operator to grade a worksite. Achieving a proper grade in a worksite operation is often a first step of the entire operation.

The discussion above is merely provided for general background information and is not intended to be used as an aid in determining the scope of the claimed subject matter.

SUMMARY

A mobile work machine includes a frame and a ground engaging element movably supported by the frame and driven by an engine to drive movement of the mobile work machine. The mobile work machine includes a movable element movably supported by the frame to move relative to the frame and an actuator coupled to the movable element to controllably drive movement of the movable element. The mobile work machine includes a sensor that detects an operation characteristic and generates a sensor signal, indicative of the operation characteristic and a grade control system that receives the sensor signal from the sensor and determines a spillage metric, based on the sensor signal. The mobile work machine also includes a control system that generates an actuator control signal based on the spillage metric. The control signal is indicative of a commanded movement of the actuator. The control system controls the actuator to perform the commanded movement.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

In carrying out a worksite operation, it may be desired to grade the worksite quickly. As an operator attempts to grade a worksite quickly, by taking deeper or longer cuts, their efficiency may go down. This can be due to a number of different problems, including excess spillage. Spillage is the material being pushed outward on either side of a work machine, and not being pushed in the direction of travel. Spillage generally forms piles or windrows on either side of a work machine, and to achieve a proper flat grade these windrows of spillage must again be moved. Further, in some instances, taking too deep or long of a cut can halt a forward movement of the work machine while the tracks of the machine are still moving, causing the tracks of the machine to dig into the worksite surface. This dig-in area will also have to be graded a second time to achieve a proper flat grade. Accordingly, the present description is directed to a system that helps detect and avoid excess spillage or other grading inefficiencies, such as dig-ins.

Figure 1:
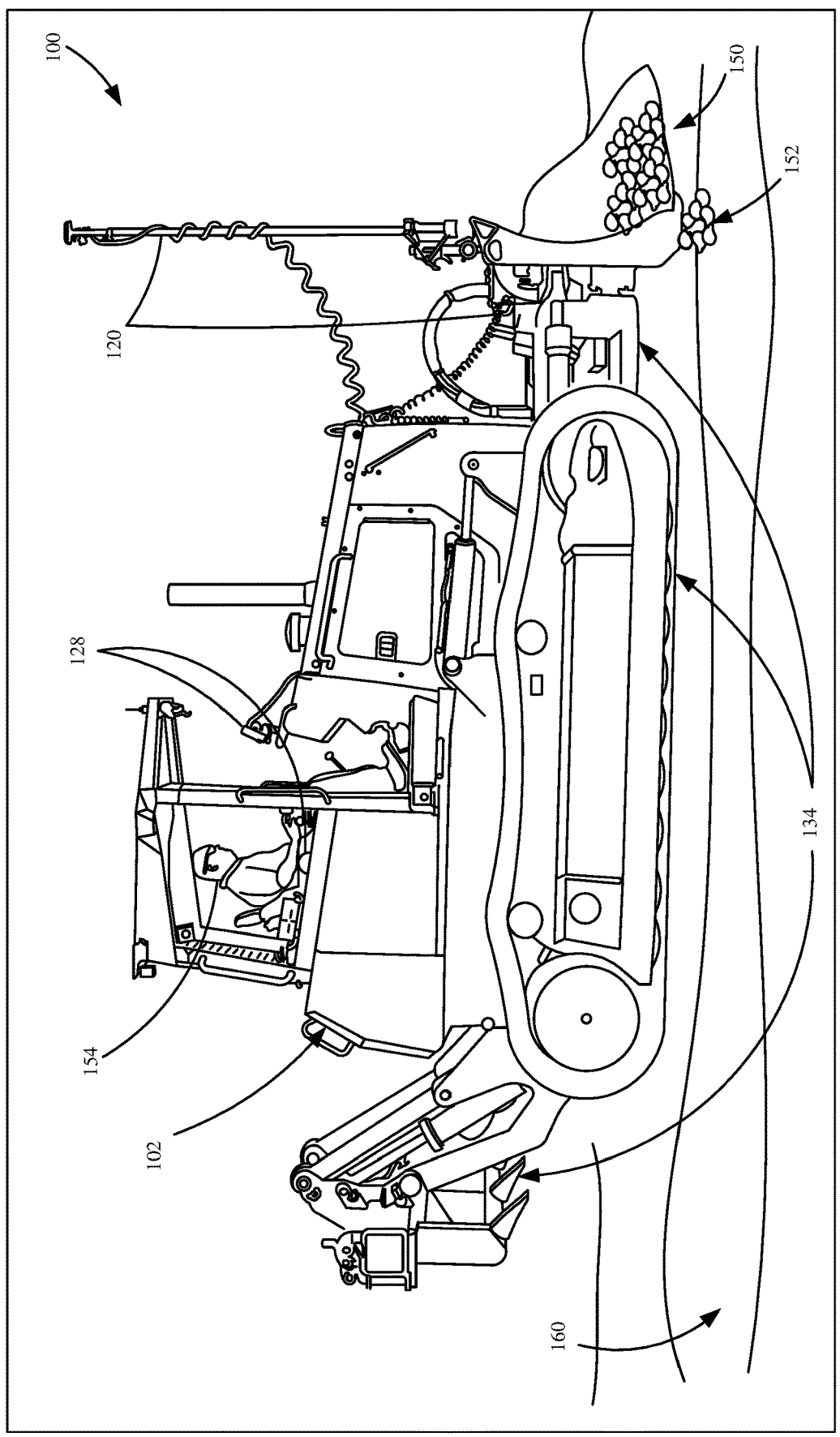
FIG. 1 is a perspective view of one example of a work machine in a worksite environment.

FIG. 1 illustrates an example of a worksite. Worksite 100 comprises a work machine 102 that operates to grade or alter surface 160. During this operation, work machine 102 cuts into surface 160 creating aggregate 150. As work machine 102 moves across surface 160, excess aggregate 150 accumulates in front of the blade of the work machine 102. At some point after the aggregate 150 begins to accumulate, the excess aggregate 150 spills around the sides of the work machine 102 where it becomes spillage 152 (forming windrows or piles of spillage). Spillage 152 can be indicative of inefficient grading operations, as this spillage 152 will have to be moved an additional time by work machine 102 to achieve a proper grade.

Work machine 102 is often operated by an operator 154. However, in some instances, machine 102 may operate at different levels of autonomy. Operator 154 utilizes a user interface 129 to operate the work machine 102. User interface 129 can comprise physical mechanisms (e.g. levers, pedals, etc.), displays, touchscreens, software interfaces, etc. to allow operator 154 to control various controllable subsystems 134 of the work machine 102. Some examples of subsystems on a work machine 102 are blade 136, steering/propulsion system 138, ripper 140, etc. To aid in operation of work machine 102 there may be sensors 120 to monitor various aspects of operation. Some examples of sensors 120 include visual sensors, hydraulic strain gauges, pressure gauges, linear displacement transducers, hall effect sensors, potentiometers, odometers, fuel gauges, GPS receivers, compasses, gyroscopes, accelerometers, etc.

Figure 2:
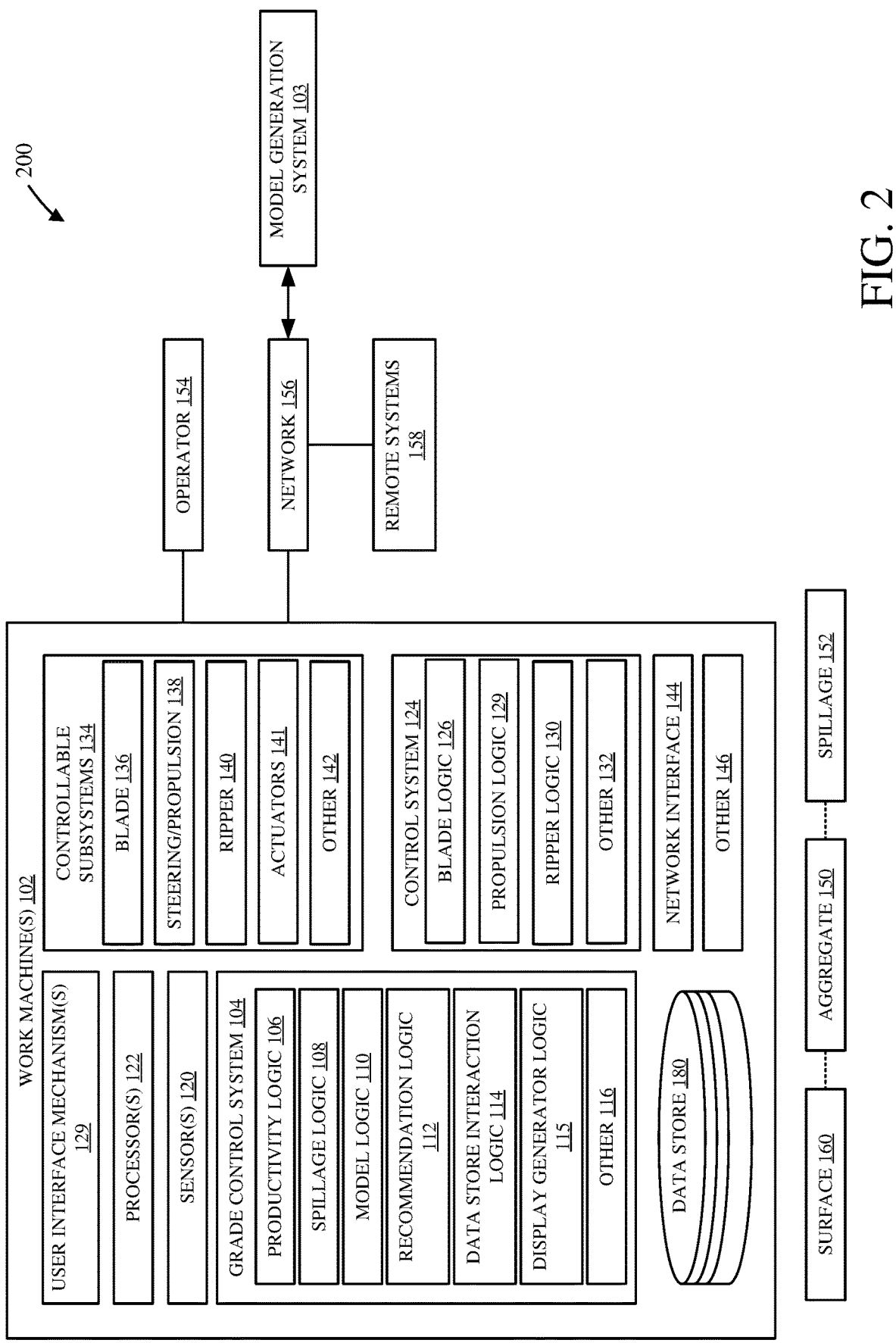
FIG. 2 is a block diagram showing one example of an operating environment.

FIG. 2 is a block diagram of one example of a worksite 100. Some components shown in FIG. 2 are similar to those shown in FIG. 1 and they are similarly numbered. Work machine 102 can also be coupled to model generation system 103 and one or more remote systems 158 over network 156. Network 156 can be any of a wide variety of different networks, such as a wide area network, a local area network, a nearfield communication network, a cellular network or other networks or combinations of networks. Before going into detail of components in worksite 100, the components of work machine 102 will be described in greater detail.

Work machine 102 comprises grade control system 104, sensor(s) 120, processor(s) 122, control system 124, user interface mechanism(s) 129, controllable subsystems 134, network interface 144, datastore 180 and may comprise other elements as well, as indicated by block 146.

It is through user interface mechanism(s) 129 that an operator 154 operates and communicates with work machine 102. User interface mechanism(s) 129 can include mechanical devices (e.g., steering wheel, levers or pedals), electronic devices (e.g., displays, joysticks, and touchscreens), haptic and audio devices, etc.

Controllable subsystems 134 include blade 136, ripper 140, steering/propulsion 138 and can include other systems as well as indicated by block 142. The actuators 141 that control the functions of controllable subsystems 134 may be controlled by signals generated from control system 124. Specifically, blade logic 126 generates control signals for the actuators 141 that move blade 136. Some examples of control signals generated by blade logic 126 include signals that control actuator 141 to raise or lower blade 136, tilt blade 136 or angle blade 136. Propulsion logic 128 generates control signals to control actuators 141 corresponding to steering/propulsion systems 138. Some examples of control signals generated by propulsion logic 128 include signals that control actuators 141 to move machine 102 forward or backward, turn or rotate machine 102, etc.

Work machine 102 can include several different sensors 120, including blade height sensor 121, blade angle sensor 123, surface sensors 125 and can include other sensors as well, as indicated by block 127. Blade height sensor 121 and blade angle sensor 123 can include different types of sensors. For instance, the sensors can include potentiometers, Hall effect sensors, etc. Surface sensors 125 include sensors that are able to detect characteristics of the worksite surface 160. Some characteristics include compactness/hardness, soil type, moisture, etc.

Grade control system 104 provides several different functions through various logic components, explained below. These logic components include productivity logic 106, spillage logic 108, recommendation logic 112 and other logic 116. The functions of grade control system 104 and its sub components may be executed by processor(s) 122.

Productivity logic 106 determines or calculates a productivity metric for work machine 102. For instance, a productivity metric can be a metric indicative of the amount of aggregate 150 currently being moved by work machine 102 or moved over a period of time. In one example, productivity logic 106 utilizes sensors 120 to determine the amount of aggregate 150 being moved by machine 102. In another example, productivity logic 106 utilizes model information from data store 180 to determine the amount of aggregate 150 being moved by machine 102. For instance, productivity logic 106 can receive operating parameters of the current operation and compare the current parameters to a table of previous operating parameters (e.g. a table of previously generated parameters). Once a similar set of previous operating parameters are identified as being close to the current operating parameters, productivity logic 106 retrieves the productivity values that the previous operating parameters produced and estimates that the current operating parameters will produce similar productivity values. This is just one example.

Spillage logic 108 determines or calculates the amount of spillage accumulated during operation of work machine 102. In one example, spillage logic 108 utilizes models from data store 180 to determine the amount of spillage. A model can contain information indicative of past spillage results and the machine and environmental variables that led to those spillage results. Spillage logic 108 can choose a model that has the closest machine and environmental variables to those of the current conditions and estimate a spillage based on the model results. For instance, spillage logic 108 receives operating parameters of the current operation and compares the current parameters to a table of previous operating parameters (e.g. a table of previously generated parameters). Once a similar set of previous operating parameters are identified as being close to the current operating parameters, spillage logic 108 retrieves the spillage values that the previous operating parameters produced in estimates that the current operating parameters will produce similar spillage values. This is one example.

In one example, spillage logic 108 utilizes sensors 120 to determine the amount of spillage 152. The sensors 120, in one example, can be one or more optical sensors that view to the sides or to the rear of work machine 120. As spillage 152 begins to accumulate, windrows of spillage 152 are formed. The windrows of spillage 152 have different visual characteristics than the surface 160 that they are formed on, which allows spillage logic 108 to identify and estimate an amount of spillage 152 in an image captured by a sensor 120, which may be, for example, an optical sensor.

Recommendation logic 112 receives outputs from other logic components and generates, for operator 154, a recommendation to improve worksite operations (e.g. time/work efficiency, fuel efficiency, component wear). Recommendation logic 112 can receive environmental or operating data and cross reference this with a model in data store 180. If the current productivity is below a given threshold, a recommendation can be generated to increase the current productivity.

Model logic 110 generates models of operation based on various worksite variables. Information generated by model logic 110 can be stored in data store 180 for later usage. Models can also be generated by a separate model generation system 103. Functions of model logic 110 and/or model generation system 103 are explained in greater detail below in the description of FIG. 4.

Datastore interaction logic 114 retrieves and stores information in Datastore 180. Some examples of information stored in data store 180 include model information, machine information, etc.

Figure 3:
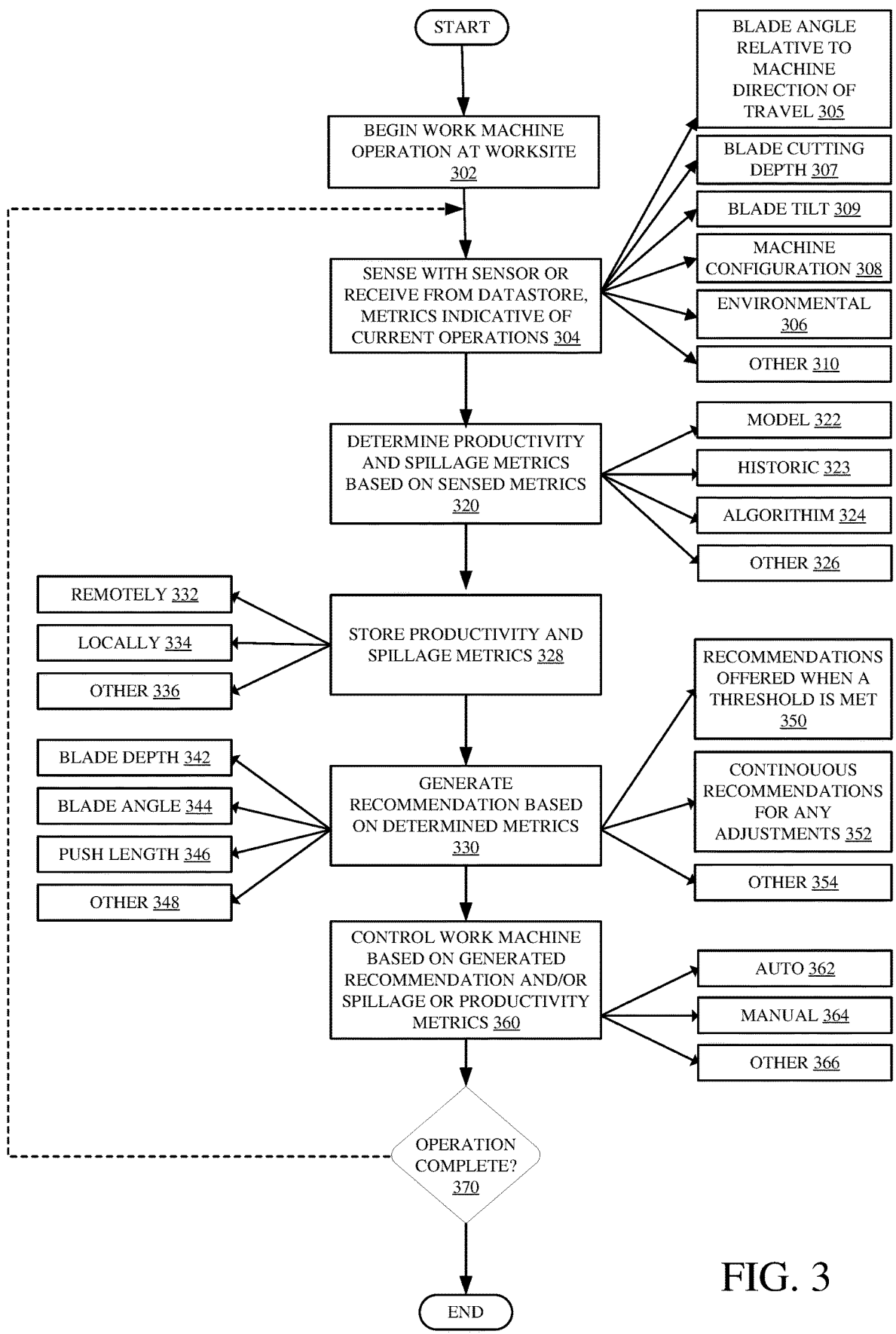
FIG. 3 is a flow diagram showing of one example of the operation of the machine.

FIG. 3 illustrates an example of controlling the operation of machine 102 at a worksite, based on the spillage metric. At block 302, the grading operation at a worksite begins. At block 304, sensors sense variables indicative of current operations as well as environmental factors. For instance, blade position relative to the machine 102 can be sensed. Blade position can include metrics such as: blade angle relative to machine direction of travel, as indicated by blade 305, blade cutting depth (height relative to frame or ground) as indicated by block 307, blade tilt, as indicated by block 309, etc. As indicated by block 308, the machine configuration can be sensed or retrieved from a datastore. Machine configuration data can include data such as: blade width, blade shape, blade capacity, machine weight, ground engaging element type (wheel, rubber track, steel tracks, etc.), ground engaging element width, etc. As indicated by block 306, environmental factors can be included in the sensed variables. Some examples of sensed environmental variables include soil type, soil moisture, soil density, soil compactness/hardness, etc. Other metrics may be sensed or retrieved as well, as indicated by block 310.

At block 320, productivity logic 106 determines productivity metrics and spillage logic 108 determines spillage metrics based on the sensed or received variables. The productivity and spillage metrics can be determined by accessing a model, as indicated by block 322. For instance, a model generated under similar conditions as those currently sensed at block 304, can be used to estimate productivity and spillage metrics. An example method of generating a model is provided in FIG. 4. The productivity and spillage metrics can be determined by accessing historic values for those metrics that were measured under similar conditions. This is indicated by block 323. Further, as indicated by block 324, the variables sensed at block 304 can be used as the inputs to an algorithm that outputs productivity and/or spillage metrics. One example algorithm for productivity may be distance traveled multiplied by blade width multiplied by blade depth of the cut minus blade spillage. Another example algorithm for determining spillage may be distance traveled multiplied by blade width multiplied by blade depth multiplied by a spillage factor, where the spillage factor is a variable generated through model analysis. The productivity and spillage metrics can be determined in other ways as well, as indicated by block 326.

At block 328, productivity and spillage metrics are optionally stored or saved. Using network interface 144, the calculated productivity and spillage values from block 320 can be sent to remote systems 158, as indicated by block 332. Productivity and spillage metrics can also be stored locally in a data store 180 by data store interaction logic 114, as indicated by block 334. Productivity and spillage metrics can be used in other ways as well, as indicated by block 336. For instance, the metrics and the operating conditions that produced them can be sent to a remote system 158 where they are added into a database of operating models. They can be used in a machine learning system to improve models, etc.

At block 340, recommendation logic 112 generates a recommendation to improve worksite operations based on the current operations and productivity/spillage metrics. As indicated by block 350, recommendation logic 112 can generate a recommendation if the productivity metric or spillage metric reaches a certain threshold. For instance, if spillage passes a maximum spillage threshold then recommendation logic 112 will generate a recommendation to reduce or prevent further spillage. As indicated by block 352, recommendation logic 112 can continually generate minor adjustment recommendations regardless of a threshold. Recommendation logic 112 can generate recommendations under other circumstances as well, as indicated by block 354.

Some examples of recommendations that can be made are indicated by blocks 342-348. As indicated by block 342, blade depth can be changed to take a shallower cut which will reduce the amount of aggregate 150 being moved and spillage 152 being accumulated. As indicated by block 344, the blade angle can be changed to direct spillage 152 to one side of work machine 102. For example, a side where it is more easily moved on a second pass or a side that may correspond to a perimeter of the area needing to be graded and therefore spillage on the given side can be tolerated. As indicated by block 346, the push length, that is the distance of each pass, can be recommended to change. For instance, the shorter the pass length, the less spillage 152 that can accumulate. Other recommendations can be made as well, as indicated by block 348. As other examples, changes in blade tilt, driving speed, steering, etc. can be recommended.

At block 360, control system 124 modifies the operation of work machine 102 based on the spillage metric, the productivity metric and/or the generated recommendation. As indicated by block 362, the work machine 102 can be controlled automatically by control system 124. As indicated by block 364, the work machine 102 can be controlled manually by the operator 154. For instance, the recommendation can be displayed on a display user interface mechanisms 129, which the operator 154 can choose to implement or not. As indicated by block 366, the machine 102 can be controlled in other ways as well.

At block 370, if the grading operation is complete, operation 300 ends. If the grading option is not complete, then operation returns to block 304 where the current conditions are sensed and productivity spillage metrics are generated, etc.

Figure 4:
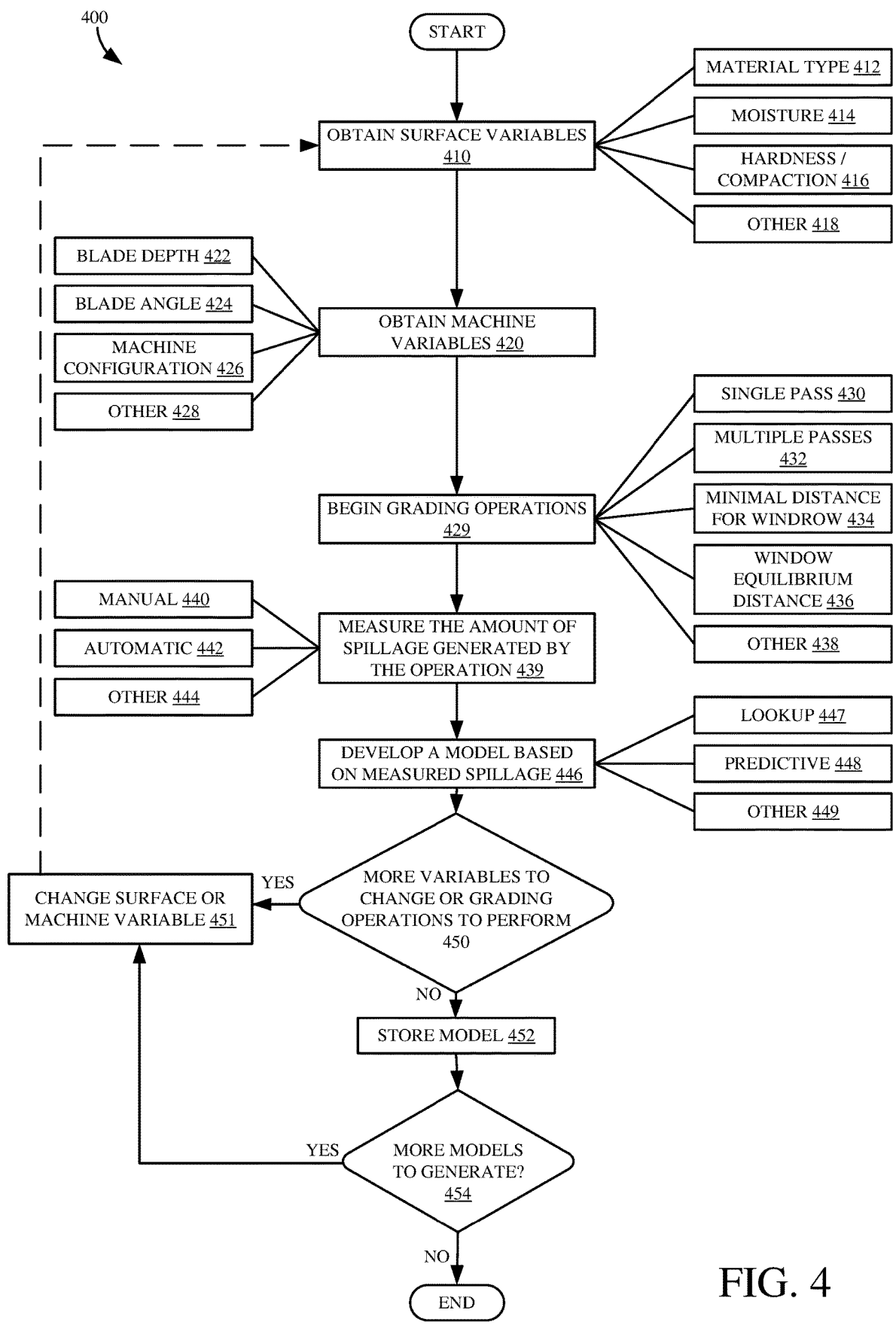
FIG. 4 is a flow diagram showing one example of the operation of the machine in performing calibration.

FIG. 4 illustrates an example of the operation of model generation system 103 and/or model logic 110 in generating a grading operation model. Operation 400 begins at block 410 where values indicative of characteristics of the worksite surface 160 are obtained. They can be sensed or input by an operator or retrieved from memory or obtained in other ways. Some examples of surface characteristics include material type as indicated by block 412, moisture as indicated by block 414, compactness/hardness as indicated by block 416. Other characteristics can be sensed or received as well as indicated by block 418.

At block 420 values indicative of characteristics of the work machine 102 are obtained. They can be sensed, input by an operator, retrieved from memory, etc. One characteristic of work machine 102 is blade depth relative to the frame of work machine 102, as indicated by block 422. Blade angle relative to the direction of travel is another characteristic of work machine 102 that can be sensed or received, as indicated by block 424. The width of the blade is another characteristic of work machine 102 that can be sensed or received. This is indicated by block 426. Of course, other characteristics of work machine 102 can be sensed or received as well, as indicated by block 428.

At block 429, work machine 102 begins grading operations on worksite surface 160. A variety of different operations can be completed in order to generate a grading model. Some of these operations are indicated by blocks 430 to 438. Block 430 indicates that a single pass across work surface 160 can be made. Block 432 indicates that multiple passes can be identified across work surface 160. Block 434 indicates that a minimal windrow distance can be made across work surface 160. A minimal windrow distance is the distance work machine 102 must travel (with given machine settings, e.g. blade depth and angle) to begin forming a windrow of spillage 152. Block 436 indicates that an operation that measures windrow equilibrium distance can be made across work surface 160. Windrow equilibrium distance is a distance work machine 102 must travel before the windrows of spillage 152 on either side of the work machine 102 are created at a constant size. For example, when windrows of spillage 152 first begin to form they are small but gradually get larger until they reach a point of substantial equilibrium (assuming no machine settings have changed). A combination of some or all of these operations can also be used.

At block 439, the amount of spillage 152, as a result of worksite operation in block 439, is measured. Measuring the amount of spillage can be completed manually as indicated by block 440. For example, the windrows of spillage 152 can be collected and weighed or otherwise measured. Measuring the amount of spillage can be completed automatically, as indicated by block 442. For example, a camera or lidar system along with image processing and volume estimation, can determine the volume of spillage 152 on the worksite 100. Measuring the amount of spillage can be completed in other ways as well, as indicated by block 444.

At block 446, model logic 110 develops a model based upon the amount of spillage from 439 and the values obtained in blocks 410, 420. The models generated can be lookup models as indicated by block 447. Lookup models, for example, can include a lookup table. The lookup table may index the amount of spillage and/or a productivity value based on machine settings, material type, push distance, among other index values. Each lookup model can be generated by changing a machine setting or surface variable and repeating operation 400 where the spillage is measured and recorded and indexed by the new machine settings or surface variables.

The models can be predictive models as indicated by block 448. Lookup models can be limited by the number of models generated under different conditions. For instance, a new lookup value for spillage and/or productivity is generated for each set of machine variables and surface variables. Predictive models can fill in the gaps between lookup models using predictive techniques such as interpolation. Models can be generated in other ways as well, as indicated by block 449.

At block 450, model generation system 103 determines whether there are more variables to change or more grading operations to perform in generating the present model. If so, a surface or machine variable is changed (as indicated by block 451) and operation 400 begins again to generate another spillage and/or productivity value under the new conditions. If at block 450, it is determined that the present model is finished, then the model is stored as indicated by block 452 and model generation system 103 determines whether more models are to be generated, as indicated by block 454. If so, processing again proceeds to block 451 where a new group of variables are set. For example, a first model may first be generated with a first group of settings, then a second model may be generated with the same settings as the first model, however the blade depth (or any setting) is changed slightly. This continues until a desired set of models is obtained.

Figure 5A:
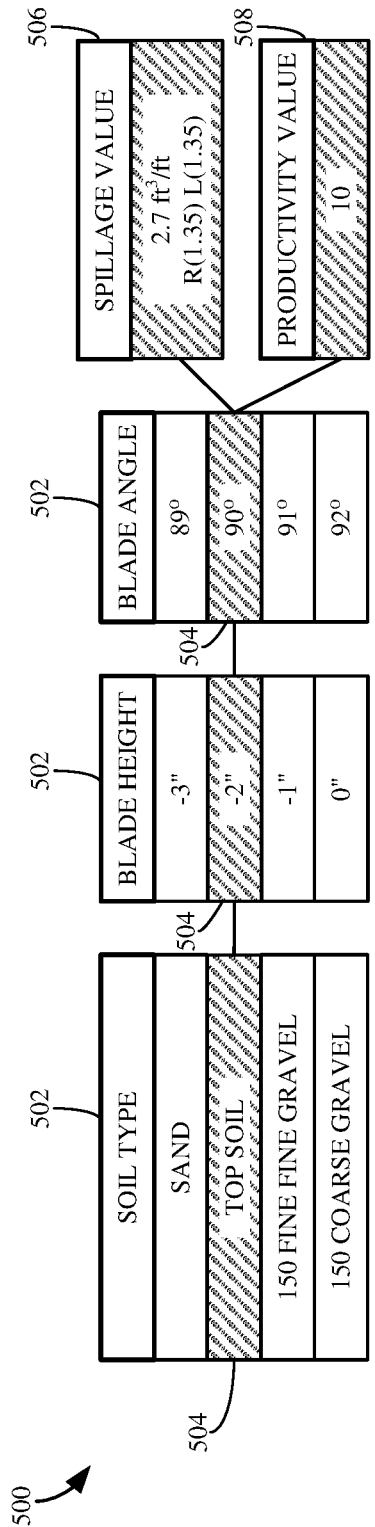
FIGS. 5A-5B show examples of spillage and productivity lookup tables.
Figure 5B:
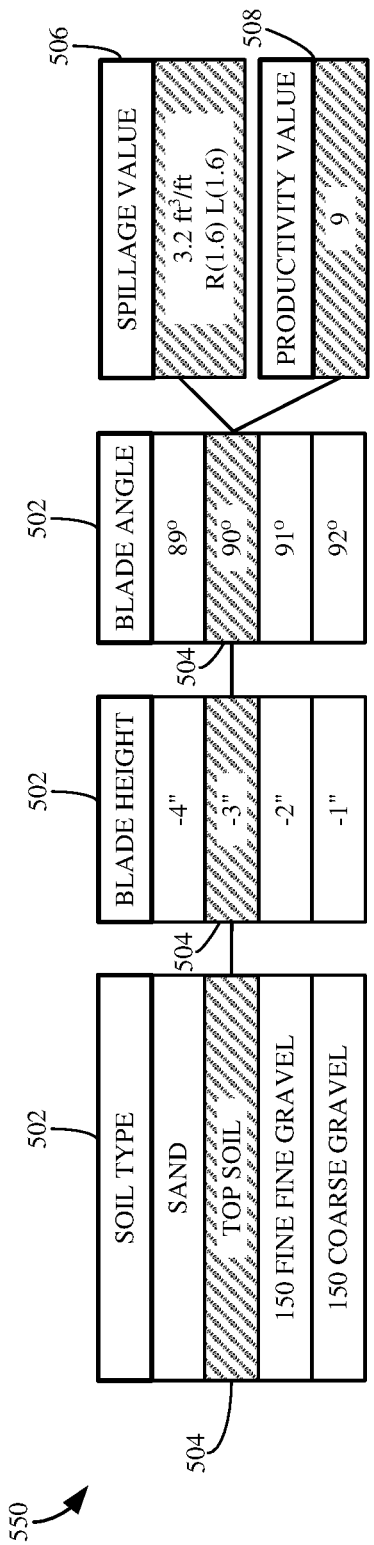

FIGS. 5A and 5B show examples of adaptive database lookup tables 500 and 550, respectively. As shown, there are a variety of data columns 502. Each data column 502 corresponds to an operating characteristic such as soil type, blade height, blade angle, blade width, soil moisture, blade tilt, soil density, soil hardness, soil compaction, etc. While the examples shown in FIGS. 5A and 5B show only three data columns 502, in other examples there may be a different number of data columns. Those shown are for the sake of example only.

The operation of models 500 and 550 is indicated by the illustrated shading. The shading shows the selected values for the index variables. For example, in FIG. 5A the selected soil type in model 500 is top soil, the selected blade height relative to the ground is −2 inches, the blade angle of the long axis of the cutting edge of the blade relative to the frame of the machine is 90 degrees. Based on the selected values in column 504, spillage logic 108 estimates that the spillage value 506 will be 2.7 cubic feet of spillage for every foot forward that the machine travels with these settings. Spillage logic 108 also estimates that the spillage will be equally distributed on both the left and right sides of the blade. Also, based on the selected values in column 504, productivity logic 106 estimates that productivity value 508 will be 10.

If any selected column value changes, spillage logic 108 and productivity logic 106 can recalculate the spillage value 506 and productivity value 508. For example, in the model 550 shown in FIG. 5B, the blade height value has changed from −2 inches to −3 inches (e.g. the blade has been lowered one inch) while all the other selected data column values remain unchanged. Spillage logic 108 then updates the estimated spillage value 506 based on this change, to be 3.2 cubic feet of spillage per foot traveled forward. Productivity logic 106 also updates the productivity value 508 to 9. In this specific example, it might be counterintuitive that taking a deeper cut can reduce productivity. However, when model logic 110 created a model with these settings it was measured to reduce productivity (e.g. the increase in cutting depth and earth moving also created more spillage that had to be moved a second time).

The present discussion has mentioned processors and servers. In one embodiment, the processors and servers include computer processors with associated memory and timing circuitry, not separately shown. They are functional parts of the systems or devices to which they belong and are activated by, and facilitate the functionality of the other components or items in those systems.

Alternatively, or in addition, the functionality described herein can be performed, at least in part, by one or more hardware logic components or software logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 6:
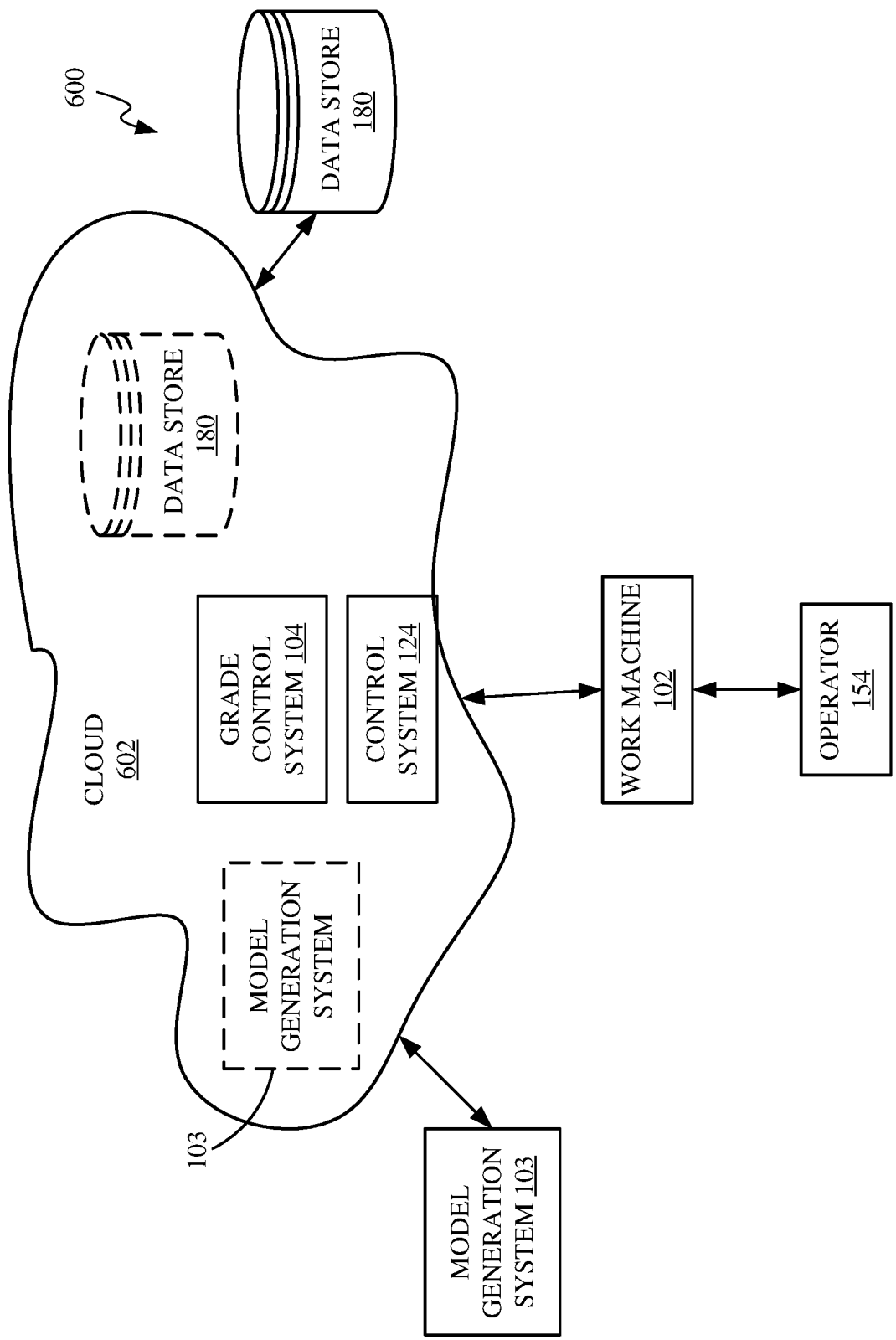
FIG. 6 shows one example of the work machine, as part of a remote server architecture.

FIG. 6 is a block diagram of work machine 102, shown in FIG. 2, except that it communicates with elements in a remote server architecture 600. In an example, remote server architecture 600 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown in FIG. 2 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the embodiment shown in FIG. 6, some items are similar to those shown in FIG. 2 and they are similarly numbered. FIG. 6 specifically shows that grade control system 104, control system 124, model generation system 103, and data store 180 can be located at a remote server location 602. Therefore, work machine 102 accesses those systems through remote server location 602.

FIG. 6 also depicts another embodiment of a remote server architecture. FIG. 6 shows that it is also contemplated that some elements of FIG. 2 are disposed at remote server location 602 while others are not. By way of example, data store 180 or model generation system 103 can be disposed at a location separate from location 602, and accessed through the remote server at location 602. Regardless of where they are located, they can be accessed directly by work machine 102, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another work machine (such as a fuel truck) can have an automated information collection system. As the work machine comes close to the fuel truck for fueling, the system automatically collects the information from the work machine using any type of ad-hoc wireless connection. The collected information can then be forwarded to the main network as the fuel truck reaches a location where there is cellular coverage (or other wireless coverage). For instance, the fuel truck can enter a covered location when traveling to fuel other machines or when at a main fuel storage location. All of these architectures are contemplated herein. Further, the information can be stored on the work machine until the work machine enters a covered location. The work machine, itself, can then send the information to the main network.

It will also be noted that the elements of FIG. 2, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 7:
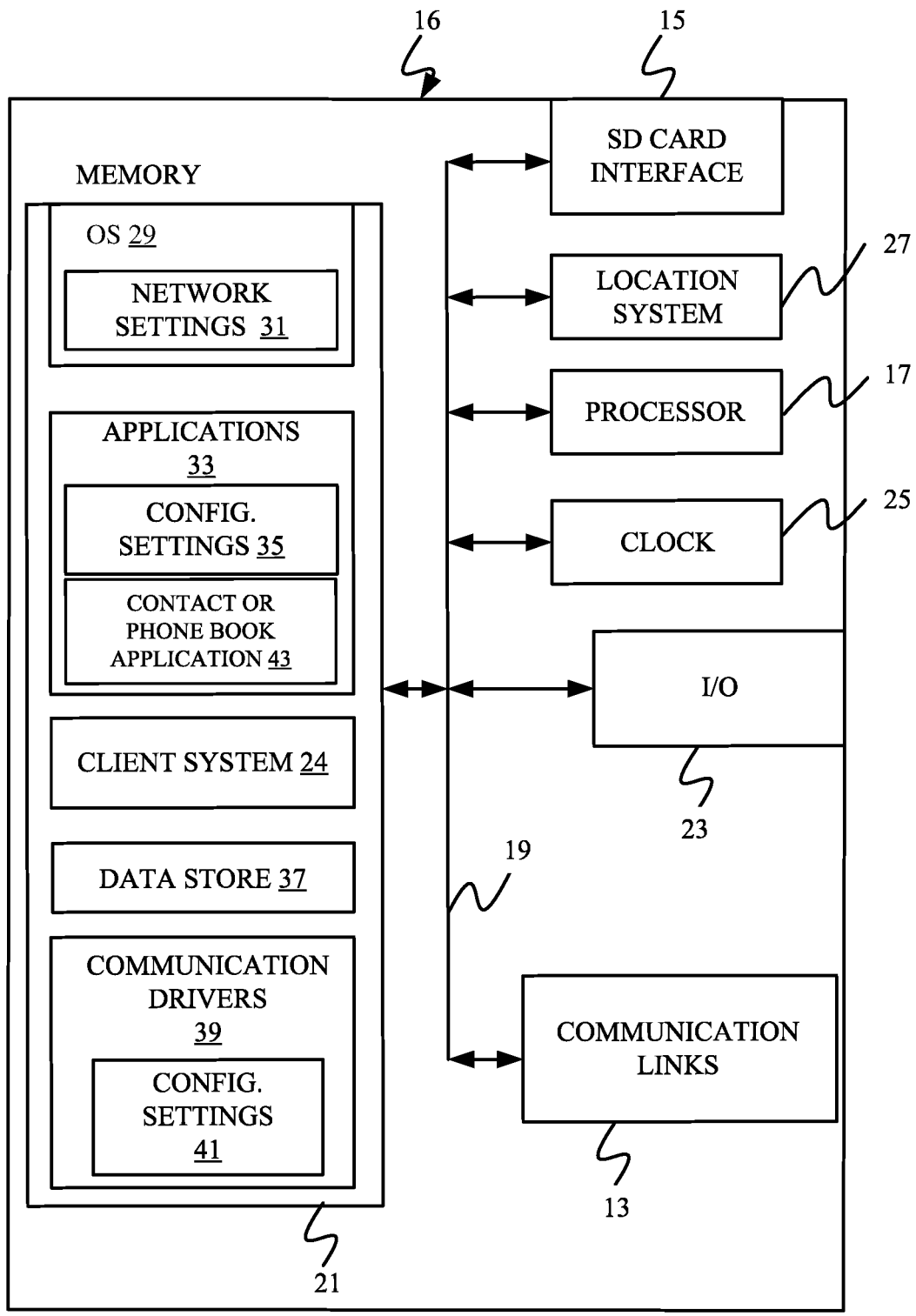
FIGS. 7-9 show examples of mobile devices that can be used with the work machine and the remote server architectures shown in the previous figures.
Figure 8:
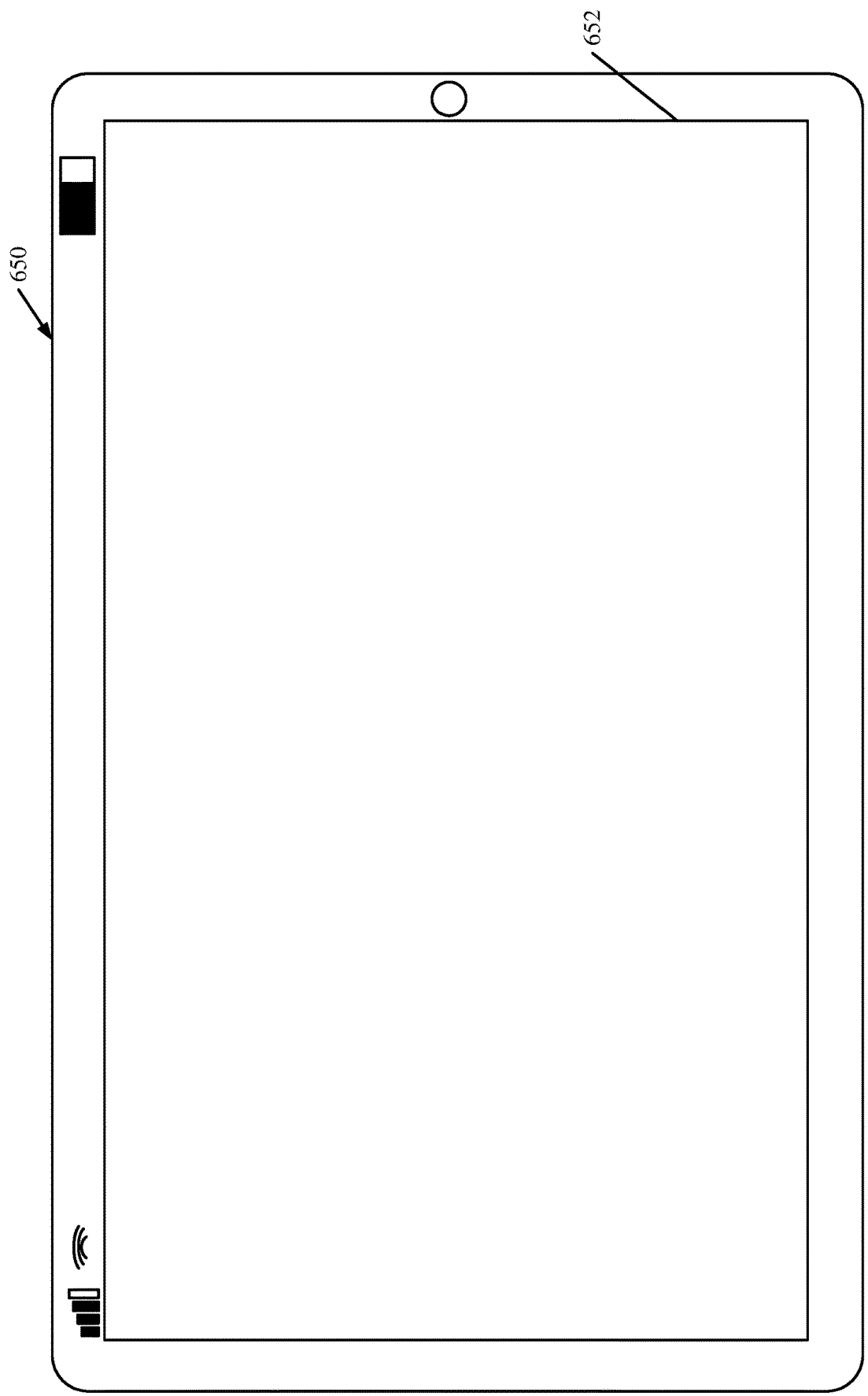
Figure 9:
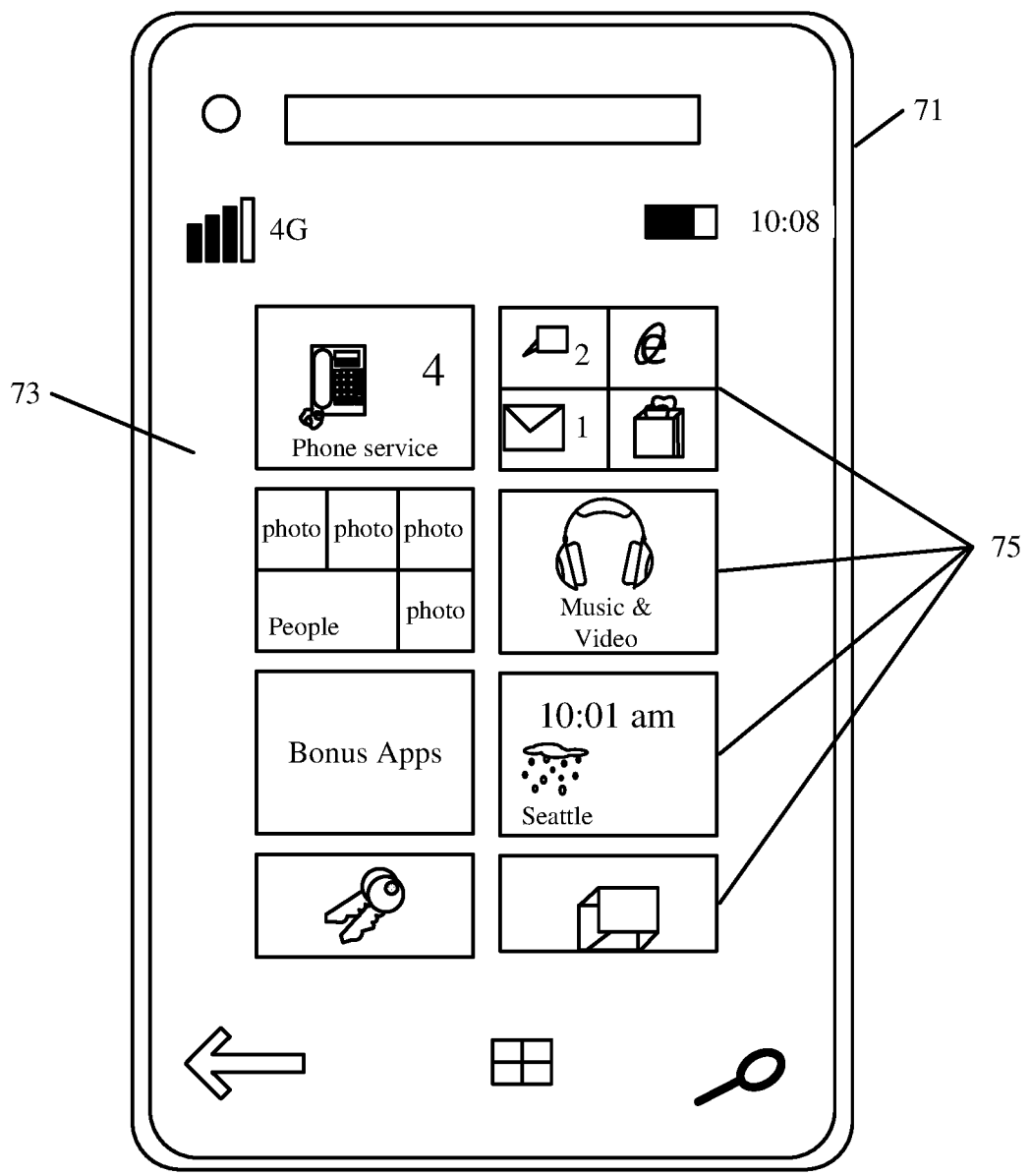

FIG. 7 is a simplified block diagram of one illustrative embodiment of a handheld or mobile computing device that can be used as a user's or client's hand held device 16, in which the present system (or parts of it) can be deployed. For instance, a mobile device can be deployed in the operator compartment of work machine 102 for use in generating, processing, or displaying the spillage and productivity metrics, the recommendations, etc. FIGS. 8-9 are examples of handheld or mobile devices.

FIG. 7 provides a general block diagram of the components of a client device 16 that can run some components shown in FIG. 2, that interacts with them, or both. In the device 16, a communications link 13 is provided that allows the handheld device to communicate with other computing devices and under some embodiments provides a channel for receiving information automatically, such as by scanning. Examples of communications link 13 include allowing communication though one or more communication protocols, such as wireless services used to provide cellular access to a network, as well as protocols that provide local wireless connections to networks.

Under other embodiments, applications can be received on a removable Secure Digital (SD) card that is connected to an interface 15. Interface 15 and communication links 13 communicate with a processor 17 (which can also embody processor 122 from FIG. 2) along a bus 19 that is also connected to memory 21 and input/output (I/O) components 23, as well as clock 25 and location system 27.

I/O components 23, in one embodiment, are provided to facilitate input and output operations. I/O components 23 for various embodiments of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. It can also include computer storage media (described below). Memory 21 stores computer readable instructions that, when executed by processor 17, cause the processor to perform computer-implemented steps or functions according to the instructions. Processor 17 can be activated by other components to facilitate their functionality as well.

FIG. 8 shows one example in which device 16 is a tablet computer 650. In FIG. 8, computer 650 is shown with user interface display screen 652. Screen 652 can be a touch screen or a pen-enabled interface that receives inputs from a pen or stylus. It can also use an on-screen virtual keyboard. Of course, it might also be attached to a keyboard or other user input device through a suitable attachment mechanism, such as a wireless link or USB port, for instance. Computer 650 can also illustratively receive voice inputs as well.

FIG. 9 provides an additional example of devices 16 that can be used, although others can be used as well. The phone in FIG. 9 is a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone. Note that other forms of the devices 16 are possible.

Figure 10:
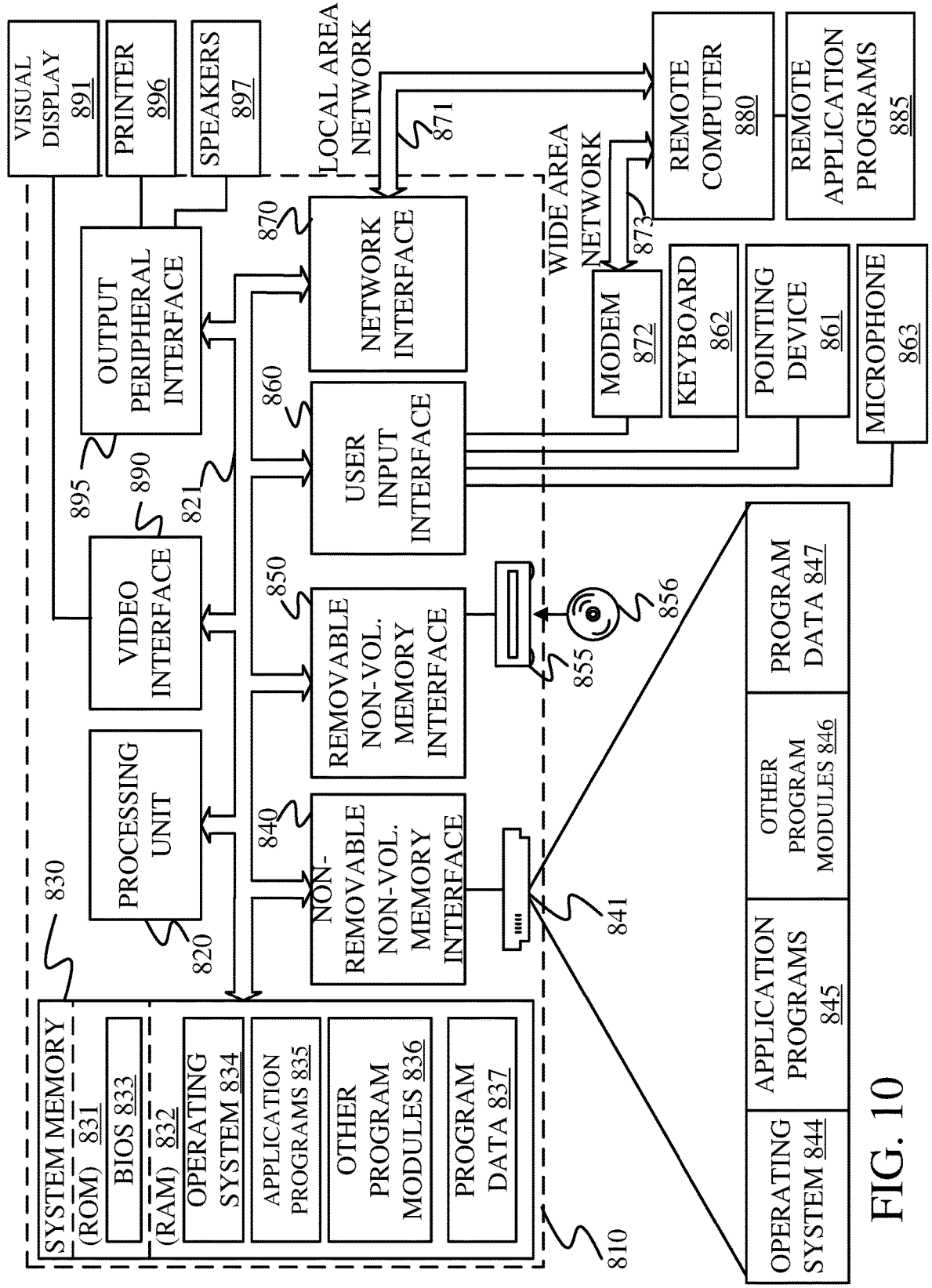
FIG. 10 is a block diagram showing one example of a computing environment that can be used in the work machine and/or in the architectures shown in the previous figures.

FIG. 10 is one example of a computing environment in which elements of FIG. 2, or parts of it, (for example) can be deployed. With reference to FIG. 10, an example system for implementing some embodiments includes a general-purpose computing device in the form of a computer 810. Components of computer 810 can include, but are not limited to, a processing unit 820 (which can comprise processor 122), a system memory 830, and a system bus 821 that couples various system components including the system memory to the processing unit 820. The system bus 821 can be any of several types of bus structures including a memory bus or memory controller, a peripheral bus, and a local bus using any of a variety of bus architectures. Memory and programs described with respect to FIG. 2 can be deployed in corresponding portions of FIG. 10.

Computer 810 typically includes a variety of computer readable media. Computer readable media can be any available media that can be accessed by computer 810 and includes both volatile and nonvolatile media, removable and non-removable media. By way of example, and not limitation, computer readable media can comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media can embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 10 illustrates operating system 834, application programs 835, other program modules 836, and program data 837.

The computer 810 can also include other removable/non-removable volatile/nonvolatile computer storage media. By way of example only, FIG. 10 illustrates a hard disk drive 841 that reads from or writes to non-removable, nonvolatile magnetic media, a magnetic disk drive 851, nonvolatile magnetic disk 852, an optical disk drive 855, and nonvolatile optical disk 856. The hard disk drive 841 is typically connected to the system bus 821 through a non-removable memory interface such as interface 840, and magnetic disk drive 851 and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 10, provide storage of computer readable instructions, data structures, program modules and other data for the computer 810. In FIG. 10, for example, hard disk drive 841 is illustrated as storing operating system 844, application programs 845, other program modules 846, and program data 847. Note that these components can either be the same as or different from operating system 834, application programs 835, other program modules 836, and program data 837.

A user can enter commands and information into the computer 810 through input devices such as a keyboard 862, a microphone 863, and a pointing device 861, such as a mouse, trackball or touch pad. Other input devices (not shown) can include a joystick, game pad, satellite dish, scanner, or the like. These and other input devices are often connected to the processing unit 820 through a user input interface 860 that is coupled to the system bus, but can be connected by other interface and bus structures. A visual display 891 or other type of display device is also connected to the system bus 821 via an interface, such as a video interface 890. In addition to the monitor, computers can also include other peripheral output devices such as speakers 897 and printer 896, which can be connected through an output peripheral interface 895.

The computer 810 is operated in a networked environment using logical connections (such as a local area network—LAN, or wide area network WAN, or a controller area network CAN) to one or more sensors or remote computers, such as a remote computer 880, or other components.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules can be stored in a remote memory storage device. FIG. 10 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Example 1 is a mobile work machine, comprising:
a frame;

a ground engaging element movably supported by the frame and driven by an engine to drive movement of the mobile work machine;

a movable grading element movably supported by the frame to move relative to the frame;

an actuator coupled to the movable grading element to controllably drive movement of the movable grading element to engage material to be graded;

a sensor that detects an operation characteristic of the mobile work machine and generates a sensor signal, indicative of the operation characteristic;

a grade control system that receives the sensor signal from the sensor and determines a spillage metric indicative of spillage of material to be graded, spilled by the movable grading element, based on the signal; and a control system that generates an actuator control signal based on the spillage metric, the actuator control signal being indicative of a commanded movement of the actuator, and wherein the control system provides the actuator control signal to control the actuator to perform the commanded movement.

Example 2 is the mobile work machine of any or all previous examples wherein the sensor comprises:

a movable grading element sensor that detects a characteristic of the movable grading element and generates a movable grading element sensor signal, indicative of the characteristic of the movable grading element and wherein the grade control system receives the movable grading element sensor signal and determines the spillage metric, based at least in part, on the movable grading element sensor signal.

Example 3 is the mobile work machine of any or all previous examples, wherein the movable grading element sensor comprises:

a position sensor that senses a characteristic indicative of a depth of engagement of the movable grading element with the material to be graded.

Example 4 is the mobile work machine of any or all previous examples, wherein the movable grading element sensor comprises:

an orientation sensor that senses an orientation of the movable grading element relative to the frame.

Example 5 is the mobile machine of any or all previous examples, wherein the grade control system determines two spillage metrics, one for each side of the mobile machine, based on the signal.

Example 6 is the mobile work machine of any or all previous examples, wherein the sensor comprises:

a surface sensor that detects a characteristic of a surface of the material to be graded and generates a surface sensor signal, indicative of the characteristic of the surface, and wherein the grade control system receives the surface sensor signal and determines the spillage metric, based at least in part, on the surface sensor signal.

Example 7 is the mobile work machine of any or all previous examples, wherein the surface sensor comprises:

a moisture sensor that senses a moisture of the material to be graded.

Example 8 is the mobile work machine of any or all previous examples, wherein the surface sensor comprises:

a surface type sensor that senses a type of material to be graded on the surface.

Example 9 is the mobile work machine of any or all previous examples, wherein the grade control system is configured to access a spillage model, indicative of a measured spillage metric measured after completing an operation on a second surface with at least one known operation characteristic, and the grade control system determines the spillage metric based on the spillage model.

Example 10 is the mobile work machine of any or all previous examples, wherein the grade control system is configured to access a spillage metric algorithm and determine the spillage metric based on the spillage metric algorithm.

Example 11 is the mobile work machine of any or all previous examples, further comprising:

a user interface display; and display generator logic that controls the user interface display to display an indication of the spillage metric.

Example 12 is the mobile work machine of any or all previous examples, further comprising:

recommendation logic that determines a recommendation based on the spillage metric;

wherein the display generator logic controls the user interface display to display the recommendation in conjunction with a user actuatable item as part of the user interface display and wherein the control system provides the actuator control signal to the actuator to control the actuator to perform the commanded movement, in response to user actuation of the user actuatable item.

Example 13 is the mobile work machine of any or all previous examples, wherein the mobile work machine comprises a bulldozer and the movable element comprises a blade.

Example 14 is a control system on a mobile work machine, comprising:

a machine sensor that detects a characteristic of the mobile work machine and generates a machine sensor signal, indicative of the characteristic of the mobile work machine;

spillage logic that receives the machine sensor signal, and determines a spillage metric based on the received machine sensor signal;

recommendation logic that receives the spillage metric and generates a recommended control change; and control logic that generates an actuator control signal, based on the recommended control change, the control signal being indicative of a recommended movement of an actuator coupled to a movable grading element to controllably drive movement of the movable grading element, and provides the actuator control signal to the actuator to control the actuator to perform the recommended movement.

Example 15 is the control system of any or all previous examples, wherein the spillage logic is configured to access a spillage lookup table and determine the spillage metric based on the spillage lookup table and machine sensor signal.

Example 16 is the control system of any or all previous examples, wherein the spillage logic is configured to access a spillage algorithm and determine the spillage metric based on the spillage algorithm and the machine sensor signal.

Example 17 is the control system of any or all previous examples, further comprising:

a surface sensor that detects a characteristic of a worksite surface and generates a surface sensor signal, indicative of the characteristic of the worksite surface, and wherein the spillage logic is configured to receive the surface sensor signal and determine the spillage metric based at least in part on the surface sensor signal.

Example 18 is the control system of any or all previous examples, wherein the surface sensor comprises a surface hardness sensor.

Example 19 is a method of controlling a work machine, the method comprising:

detecting, with a surface sensor, a characteristic of a worksite surface;

sensing, with a machine setting sensor, a current machine setting of the work machine;

accessing a grading model;

determining, with spillage logic, a spillage value, based on the characteristic of the worksite surface, the current machine setting and the grading model;

generating a recommendation setting with recommendation logic, based on the spillage value; and controlling the work machine with a control system to implement the recommendation setting.

Example 20 is the method of any or all previous examples, wherein detecting the characteristic of the worksite surface comprises detecting a soil type of the worksite surface, wherein sensing the current machine setting of the work machine comprises detecting a height of a movable grading element of the work machine, relative to a frame of the work machine; and wherein generating the recommendation setting comprises generating a recommended height of the movable grading element, relative to the frame of the work machine, based on the spillage value.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A mobile work machine, comprising:
a frame;
a ground engaging element movably supported by the frame and driven by an engine to drive movement of the mobile work machine;
a movable grading element movably supported by the frame to move relative to the frame;
an actuator coupled to the movable grading element to controllably drive movement of the movable grading element to engage material to be graded;
a sensor that detects an operation characteristic of the mobile work machine and generates a sensor signal, indicative of the operation characteristic;
a grade control system that receives the sensor signal from the sensor and determines a spillage metric indicative of spillage of material to be graded, spilled by the movable grading element, based on the signal; and
a control system that generates an actuator control signal based on the spillage metric, the actuator control signal being indicative of a commanded movement of the actuator, and wherein the control system provides the actuator control signal to control the actuator to perform the commanded movement.

2. The mobile work machine of claim 1, wherein the sensor comprises:
a movable grading element sensor that detects a characteristic of the movable grading element and generates a movable grading element sensor signal, indicative of the characteristic of the movable grading element and wherein the grade control system receives the movable grading element sensor signal and determines the spillage metric, based at least in part, on the movable grading element sensor signal.

3. The mobile work machine of claim 2, wherein the movable grading element sensor comprises:

a position sensor that senses a characteristic indicative of a depth of engagement of the movable grading element with the material to be graded.

4. The mobile work machine of claim 2, wherein the movable grading element sensor comprises:
an orientation sensor that senses an orientation of the movable grading element relative to the frame.

5. The mobile machine of claim 4, wherein the grade control system determines two spillage metrics, one for each side of the mobile machine, based on the signal.

6. The mobile work machine of claim 1, wherein the sensor comprises:
a surface sensor that detects a characteristic of a surface of the material to be graded and generates a surface sensor signal, indicative of the characteristic of the surface, and wherein the grade control system receives the surface sensor signal and determines the spillage metric, based at least in part, on the surface sensor signal.

7. The mobile work machine of claim 6, wherein the surface sensor comprises:
a moisture sensor that senses a moisture of the material to be graded.

8. The mobile work machine of claim 6, wherein the surface sensor comprises:
a surface type sensor that senses a type of material to be graded on the surface.

9. The mobile work machine of claim 1, wherein the grade control system is configured to access a spillage model, indicative of a measured spillage metric measured after completing an operation on a second surface with at least one known operation characteristic, and the grade control system determines the spillage metric based on the spillage model.

10. The mobile work machine of claim 1, wherein the grade control system is configured to access a spillage metric algorithm and determine the spillage metric based on the spillage metric algorithm.

11. The mobile work machine of claim 1, further comprising:
a user interface display; and
display generator logic that controls the user interface display to display an indication of the spillage metric.

12. The mobile work machine of claim 11, further comprising:
recommendation logic that determines a recommendation based on the spillage metric;
wherein the display generator logic controls the user interface display to display the recommendation in conjunction with a user actuatable item as part of the user interface display and wherein the control system provides the actuator control signal to the actuator to control the actuator to perform the commanded movement, in response to user actuation of the user actuatable item.

13. The mobile work machine of claim 1, wherein the mobile work machine comprises a bulldozer and the movable element comprises a blade.

14. A control system on a mobile work machine, comprising:
a machine sensor that detects a characteristic of the mobile work machine and generates a machine sensor signal, indicative of the characteristic of the mobile work machine;
spillage logic that receives the machine sensor signal, and determines a spillage metric based on the received machine sensor signal;

recommendation logic that receives the spillage metric and generates a recommended control change; and control logic that generates an actuator control signal, based on the recommended control change, the control signal being indicative of a recommended movement of an actuator coupled to a movable grading element to controllably drive movement of the movable grading element, and provides the actuator control signal to the actuator to control the actuator to perform the recommended movement.

15. The control system of claim 14, wherein the spillage logic is configured to access a spillage lookup table and determine the spillage metric based on the spillage lookup table and machine sensor signal.

16. The control system of claim 14, wherein the spillage logic is configured to access a spillage algorithm and determine the spillage metric based on the spillage algorithm and the machine sensor signal.

17. The control system of claim 14, further comprising:
a surface sensor that detects a characteristic of a worksite surface and generates a surface sensor signal, indicative of the characteristic of the worksite surface, and wherein the spillage logic is configured to receive the surface sensor signal and determine the spillage metric based at least in part on the surface sensor signal.

18. The control system of claim 17, wherein the surface sensor comprises a surface hardness sensor.

19. A method of controlling a work machine, the method comprising:
detecting, with a surface sensor, a characteristic of a worksite surface;
sensing, with a machine setting sensor, a current machine setting of the work machine;
accessing a grading model;
determining, with spillage logic, a spillage value, based on the characteristic of the worksite surface, the current machine setting and the grading model;
generating a recommendation setting with recommendation logic, based on the spillage value; and
controlling the work machine with a control system to implement the recommendation setting.

20. The method of claim 19, wherein detecting the characteristic of the worksite surface comprises detecting a soil type of the worksite surface, wherein sensing the current machine setting of the work machine comprises detecting a height of a movable grading element of the work machine, relative to a frame of the work machine; and wherein generating the recommendation setting comprises generating a recommended height of the movable grading element, relative to the frame of the work machine, based on the spillage value.

* * * * *